United States Patent

Halstrom

[19]

[11] Patent Number: 6,161,542
[45] Date of Patent: Dec. 19, 2000

[54] METHOD OF TREATING SNORING AND OBSTRUCTIVE SLEEP APNEA

[75] Inventor: Leonard Wayne Halstrom, Lion's Bay, Canada

[73] Assignee: Silent Knights Ventures Inc., Vancouver, Canada

[21] Appl. No.: 09/362,887

[22] Filed: Jul. 29, 1999

Related U.S. Application Data

[62] Division of application No. 08/554,670, Nov. 8, 1995, which is a continuation of application No. 08/220,304, Mar. 30, 1994, which is a continuation-in-part of application No. 08/046,549, Apr. 13, 1993, Pat. No. 5,365,945.

[51] Int. Cl.[7] .................................................. A61F 5/56
[52] U.S. Cl. ........................... 128/848; 128/859; 602/902
[58] Field of Search ..................................... 128/846, 848, 128/859–862; 602/902; 433/6, 7

[56] References Cited

U.S. PATENT DOCUMENTS

| | | | |
|---|---|---|---|
| 1,146,264 | 7/1915 | Kelly | 128/861 |
| 4,901,737 | 2/1990 | Toone | 128/848 |
| 5,409,017 | 4/1995 | Lowe | 128/848 |
| 5,427,117 | 6/1995 | Thornton | 128/848 |

*Primary Examiner*—Michael A. Brown
*Attorney, Agent, or Firm*—Oyens Wiggs Green & Mutala

[57] ABSTRACT

A dentally retained intra-oral appliance worn at night for treatment of snoring and obstructive sleep apnea. The appliance maintains the patient's mandible in an anterior, protruded position to prevent obstruction of the pharyngeal airway. The appliance allows a limited degree of lateral movement of the mandible relative to the upper jaw in the protruded position to prevent aggravation of the patient's tempromandibular joint and associated muscles and ligaments. The appliance preferably consists of an upper bite block conforming to the patient's maxillary dentition, a lower bite block conforming to the patient's mandibular dentition, and a connecting assembly secured to the upper and lower bite blocks for adjustably coupling the upper and lower bite blocks together. The invention also relates to a method of treating snoring and obstructive sleep apnea using the dental appliance.

5 Claims, 5 Drawing Sheets

METHOD OF TREATING SNORING AND OBSTRUCTIVE SLEEP APNEA

This is a divisional of Ser. No. 08/554,670 filed Nov. 8, 1995, which is a continuation of Ser. No. 08/220,304 filed Mar. 30, 1994, now abandoned, which is a continuation-in-part of Ser. No. 08/046,549 filed Apr. 13, 1993 which issued as U.S. Pat. No. 5,365,945 on Nov. 22, 1994.

FIELD OF THE INVENTION

This application relates to a dentally retained intra-oral appliance worn at night for treatment of snoring and obstructive sleep apnea. The appliance maintains the patient's mandible in an anterior, protruded position to prevent obstruction of the pharyngeal airway. The appliance allows a limited degree of lateral movement of the mandible relative to the upper jaw in the protruded position to prevent aggravation of the tempromandibular joint and associated muscles and ligaments.

BACKGROUND OF THE INVENTION

Snoring and obstructive sleep apnea are typically caused by complete or partial obstruction of an individual's pharyngeal airway during sleep. Usually airway obstruction results from the apposition of the rear portion of the tongue or soft palate with the posterior pharyngeal wall. Obstructive sleep apnea is a potentially lethal disorder in which breathing stops during sleep for 10 seconds or more, sometimes up to 300 times per night. Snoring occurs when the pharyngeal airway is partially obstructed, resulting in vibration of the oral tissues during respiration. These sleep disorders tend to become more severe as patients grow older, likely due to a progressive loss of muscle tone in the patient's throat and oral tissues.

Habitual snoring and sleep apnea have been associated with other potentially serious medical conditions, such as hypertension, ischemic heart disease and strokes. Accordingly, early diagnosis and treatment is recommended. One surgical approach, known as uvulopalatopharyngoplasty, involves removal of a portion of the soft palate to prevent closure of the pharyngeal airway during sleep. However, this operation is not always effective and may result in undesirable complications, such as nasal regurgitation.

A wide variety of non-surgical approaches for treating sleep disorders have also been proposed including the use of oral cavity appliances. It has been previously recognized that movement of the mandible (lower jaw) forward relative to the maxilla (upper jaw) can eliminate or reduce sleep apnea and snoring symptoms by causing the pharyngeal air passage to remain open. Several intra-oral dental appliances have been developed which the user wears at night to fix the mandible in an anterior, protruded (i.e. forward) position. Such dental appliances essentially consist of acrylic or elastomeric bite blocks, similar to orthodontic retainers or athletic mouthguards, which are custom-fitted to the user's upper and lower teeth and which may be adjusted to vary the degree of anterior protrusion.

U.S. Pat. No. 4,901,737, which issued to Toone on Feb. 20, 1990, exemplifies the prior art. Toone discloses an intra-oral appliance for reducing snoring which repositions the mandible in an inferior (open) and anterior (protrusive) position as compared to the normally closed position of the jaw. Once the dentist or physician determines the operative "snore reduction position" for a particular patient, an appropriate mold is taken of the maxillary dentition and of the mandibular dentition for formation of the appliance template. The Toone appliance includes a pair of V-shaped spacer members formed from dental acrylic which extend between the maxillary and mandibular dentition to form a unitary mouthpiece. In an alternative embodiment of the Toone invention, the spacer members are formed in two pieces and a threaded rod is provided to enable adjustment of the degree of mandibular protrusion or retrusion after the mouthpiece is formed.

European patent application No. 0,312,368 published Apr. 19, 1989 also discloses an intra-oral device for preventing snoring. This device consists of a U-shaped mouthpiece which conforms to the upper dental arch of the user and includes a sloped, lower ramp for engaging the mandibular dentition. Normal mouth motions, such as the clenching of the jaw, will cause some of the mandibular dentition to engage the underside of the ramp, thereby camming the lower jaw forward to increase the spacing between the base of the tongue and the posterior wall of the pharynx.

While prior art dental appliances have proven effective in maintaining the mandible in a protruded position to improve airway patency, they often result in undesirable side effects. One of the most common side effects is aggravation of the tempromandibular joint and related jaw muscles and ligaments, especially in individuals who have a tendency to grind their teeth during sleep. Aggravation of the tempromandibular joint has been associated with a wide variety of physical ailments, including migraine headaches. Accordingly, many individuals suffering from sleep apnea and snoring disorders are not able to tolerate existing anti-snoring dental appliances for long periods of time.

The need has therefore arisen for a dental appliance for treatment of snoring and sleep apnea which will maintain the mandible in a preferred anterior position, but which will also allow a limited degree of lateral excursion of the mandible relative to the upper jaw to avoid discomfort to the tempromandibular joint and related muscles and ligaments.

SUMMARY OF THE INVENTION

In accordance with the invention there is provided an intra-oral dental appliance to be worn by a patient during sleep for treatment of obstructive sleep apnea and snoring. The dental appliance includes an upper member conforming to the patient's maxillary dentition, a lower member conforming to the patient's mandibular dentition, and connecting means for releasably coupling the upper and lower members together to maintain the lower member in an anterior, protruded position relative to the upper member. The connecting means includes adjusting means which is manually adjustable to incrementally vary the degree of anterior protrusion of the lower member relative to the upper member. The connecting means is loosely coupled to the lower member to permit a limited degree of lateral movement of the lower member relative to the upper member in the anterior, protruded position.

The upper and lower members are preferably flexible bite blocks formed from elastomeric material. Preferably the connecting means is secured to anterior regions of the upper and lower bite blocks and includes a first element bonded to an undersurface of the upper bite block; a second element bonded to an upper surface of the lower bite block; and an elongated connector for releasably coupling the first and second elements together.

Preferably the connector has an upper end which is fixedly connectable to the first element and a lower end which is loosely connectable to the second element to permit the limited degree of movement of the lower bite block relative to the upper bite block in the protruded position. Advantageously, the second element has an internal cavity for capturing the lower end of the connector, the cavity having an opening formed on an upper surface of the second element through which the connector extends. The connector preferably consists of a stylus having a threaded upper portion and an enlarged head formed on its lower end having a diameter exceeding the size of the cavity opening.

The upper element preferably consists of a retention plate having a plurality of internally threaded apertures formed therein for releasably receiving the threaded portion of the stylus. The threaded apertures are spaced apart at regular intervals to enable incremental adjustment of the degree of anterior protrusion of the lower bite block relative to the upper bite block.

The second element preferably consists of a guide box having an upper surface, vertical sidewalls, and an open bottom end, the guide box having a hollow area between the sidewalls comprising the internal cavity and an aperture formed on the upper surface comprising the cavity opening. The dimensions of the cavity preferably exceed the size of the stylus head and the cavity opening is laterally elongated to permit a limited degree of lateral movement of the lower bite block relative to the stylus. The guide box further includes a base plate for releasably covering the guide box bottom end, the base plate having an aperture formed therein to permit access to the stylus head captured within the internal cavity.

The retention plate and the base plate each further include a plurality of retention apertures spaced around the periphery thereof to enable acrylic to flow through the plates when the plates are initially bonded to the upper and lower bite blocks.

Preferably, the upper and lower bite blocks further include a first pair of bite pads formed on the undersurface of the upper bite block and projecting downwardly therefrom and a second pair of bite pads formed on an upper surface of the lower bite block and projecting upwardly therefrom for slidably engaging the first pair of bite pads. The bite pads are located in a posterior region of the bite blocks to limit closure of the patient's jaw.

A connecting assembly for use in an intra-oral dental appliance to be worn by a patient during sleep for treatment of obstructive sleep apnea and snoring is also disclosed, the dental appliance comprising an upper bite block conforming to the patient's maxillary dentition and a lower bite block conforming to the patient's mandibular dentition. The connecting assembly includes a first element securable to an undersurface of the upper bite block; a second element securable to an upper surface of the lower bite block; and an elongated connector for releasably coupling the first and second elements together to maintain the lower member in an anterior, protruded position relative to the upper member, the connector having an upper end which is securely connectable to the first element and a lower end which is loosely connectable to the second element to permit a limited degree of lateral movement of the lower bite block relative to the upper bite block in the protruded position.

A method of treating snoring and obstructive sleep apnea by adjustably maintaining a patient's mandible in a protruded position is also disclosed comprising the steps of (a) casting an upper bite block by taking a mold of the patient's maxillary dentition; (b) casting a lower bite block by taking a mold of the patient's mandibular dentition; (c) securing a first retention element to the undersurface of the upper bite block in an anterior region thereof; (d) securing a second retention element to an upper surface of the lower bite block in an anterior region thereof, the second element comprising an upwardly projecting connector having a lower end loosely captured within a cavity formed in the second element; (e) determining the preferred degree of mandibular protrusion required to alleviate the patient's sleep apnea and snoring symptoms; and (f) releasably securing an upper end of the connector to the first retention element at a fixed position corresponding to the patient's preferred degree of mandibular protrusion as determined in step (e).

BRIEF DESCRIPTION OF THE DRAWINGS

In drawings which illustrate the preferred embodiment of the invention.

DETAILED DESCRIPTION OF THE PREFERRED EMBODIMENT

Figure 1:
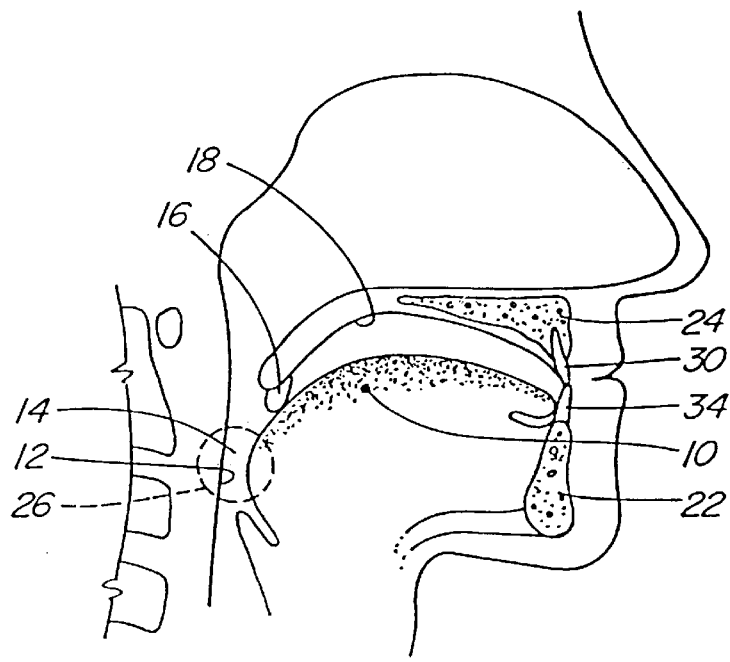
FIG. 1 is a schematic, side elevational view of the upper pharyngeal region of a typical patient suffering from obstructive sleep apnea or snoring.

FIG. 1 is a schematic, side elevational view of the upper pharyngeal region of a typical patient suffering from obstructive sleep apnea or snoring. When the patient is asleep the oral cavity tissues relax and the distal (rear) portion of the tongue 10 tends to slide rearwardly toward the posterior pharyngeal wall 12. This may result in partial or complete occlusion of the pharyngeal airway 14 in the circled region 26. As the volume of airway 14 diminishes, the velocity of the air passing the oral cavity tissues tends to increase. This may result in vibration of the oral cavity tissues, such as the uvula 16 which is a fleshy projection suspended from the soft palate 18 over the root of tongue 10. The vibration of these oral tissues causes the snoring sound.

Figure 2:
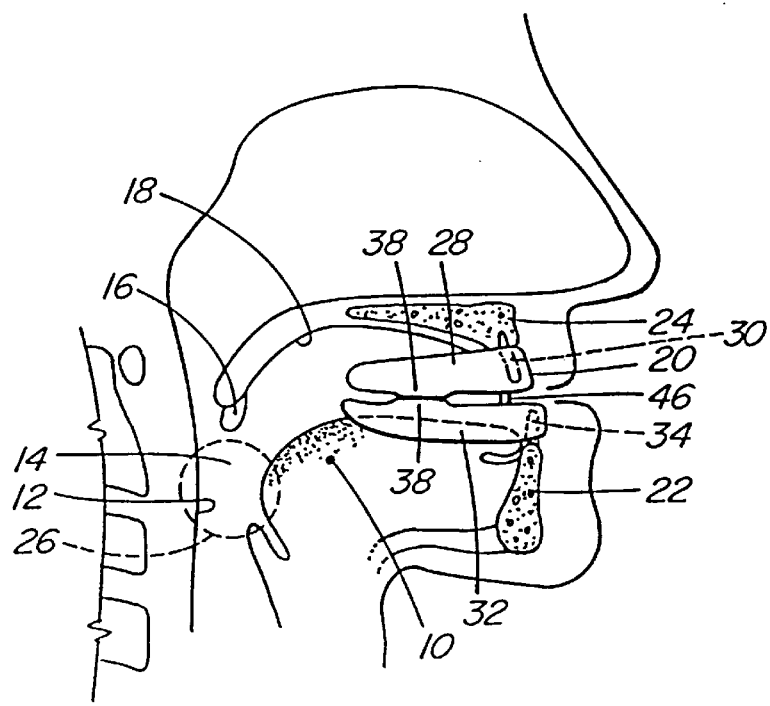
FIG. 2 is a schematic, side elevational view of the patient of FIG. 1 fitted with the applicant's dental appliance to maintain the patient's mandible in a protruded position, thereby averting obstruction of the pharyngeal airway.

FIG. 2 is a schematic, side elevational view of the individual of FIG. 1 fitted with the applicant's dental appliance 20. Dental appliance 20 causes the individual's mandible 22 to be moved to an anterior, protruded position relative to the upper jaw 24. This causes the dorsal surface of the tongue 10 to move forwardly away from the posterior pharyngeal wall 12. This in turn results in an increase in volume of the pharyngeal airway 14 as shown in the circled region 26. It has been shown that maintaining airway 14 substantially open during sleep alleviates the undesirable symptoms associated with obstructive sleep apnea and snoring.

Figure 4:
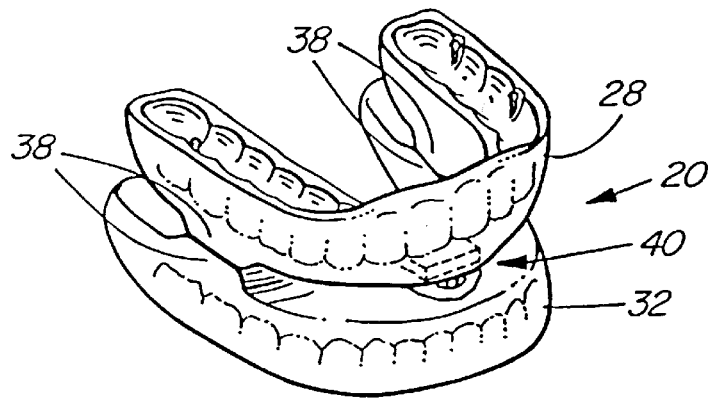
FIG. 4 is an isometric view of the applicant's dental appliance.
Figure 5:
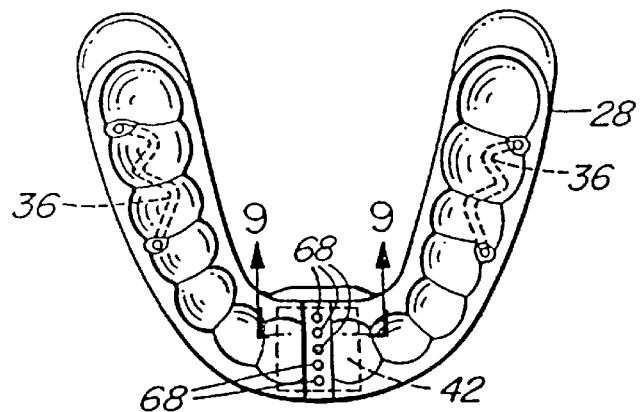
FIG. 5 is a top, plan view of the dental appliance of FIG. 4.
Figure 6:
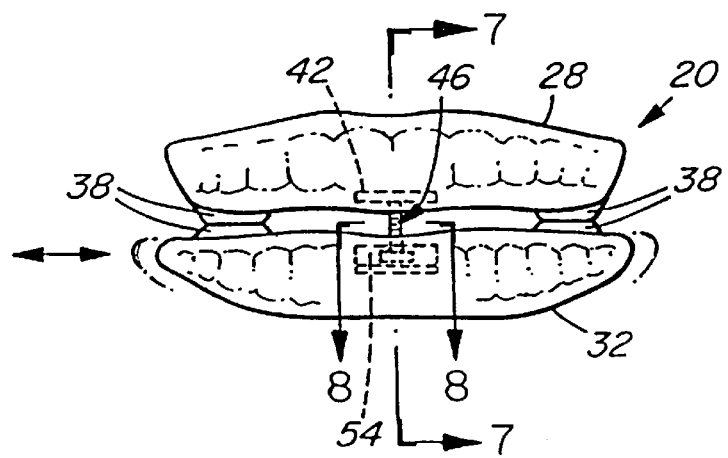
FIG. 6 is a front, elevational view of the dental appliance of FIG. 4.

FIGS. 4–6 depict the preferred structure of dental appliance 20 in further detail. Appliance 20 consists of an upper bite block 28 shaped to conform to the maxillary dentition 30 and a lower bite block 32 shaped to conform to the mandibular dentition 34. Bite blocks 28, 32 are preferably constructed from an elastomeric material. Each bite block 28, 32 includes stainless steel dental wires 36 (FIG. 5) to stabilize appliance 20 and ensure that it securely engages the wearer's teeth.

As best shown in FIGS. 4 and 6, the posterior region of each bite block 28, 32 includes hard acrylic bite pads 38 which provide a stop to the closure of the jaw and which support the wearer's tempromandibular joint as discussed further below.

Figure 3:
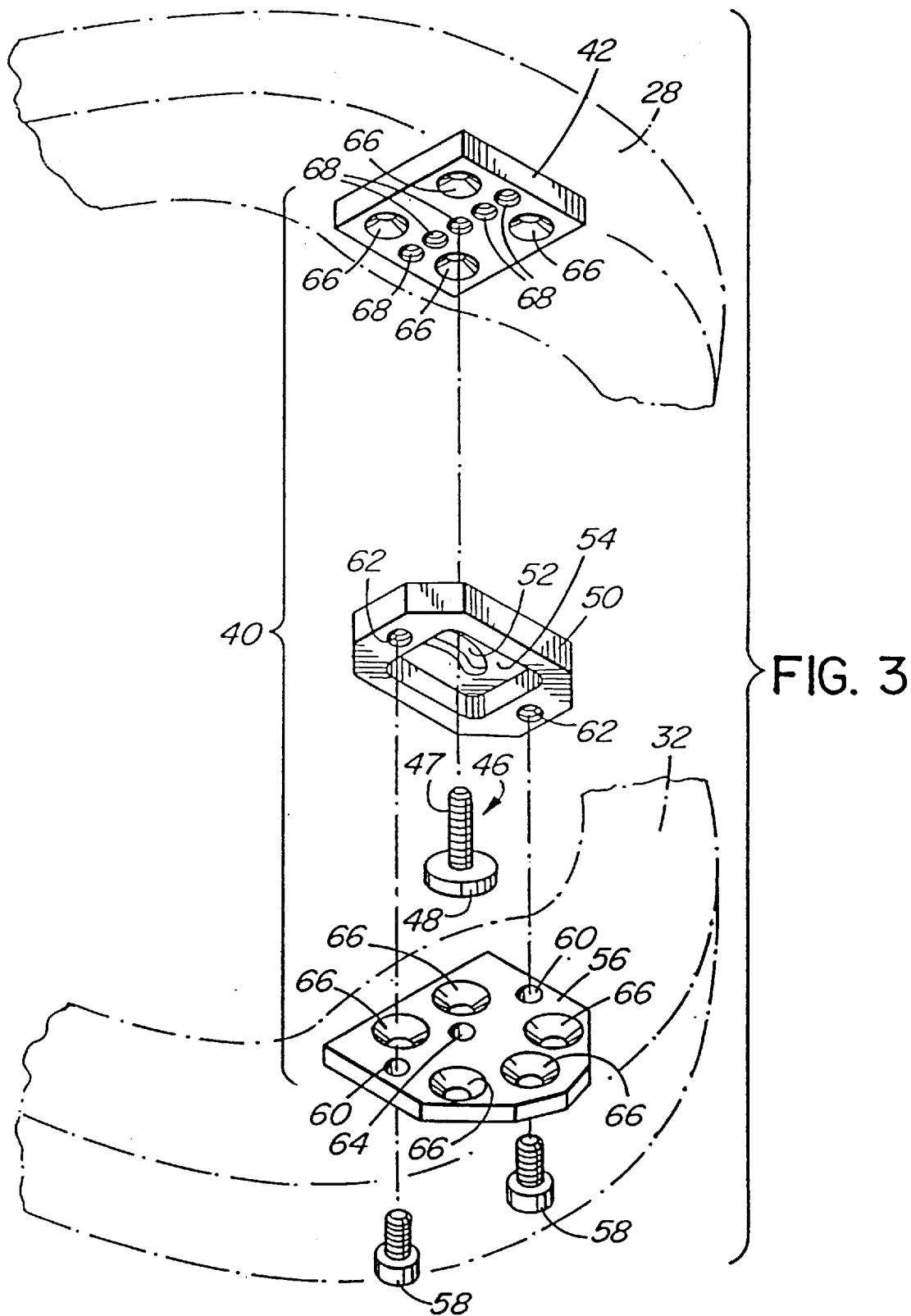
FIG. 3 is an enlarged, exploded view of the connecting assembly of the applicant's invention for connecting the upper and lower bite blocks shown in dotted outline.
Figure 9:
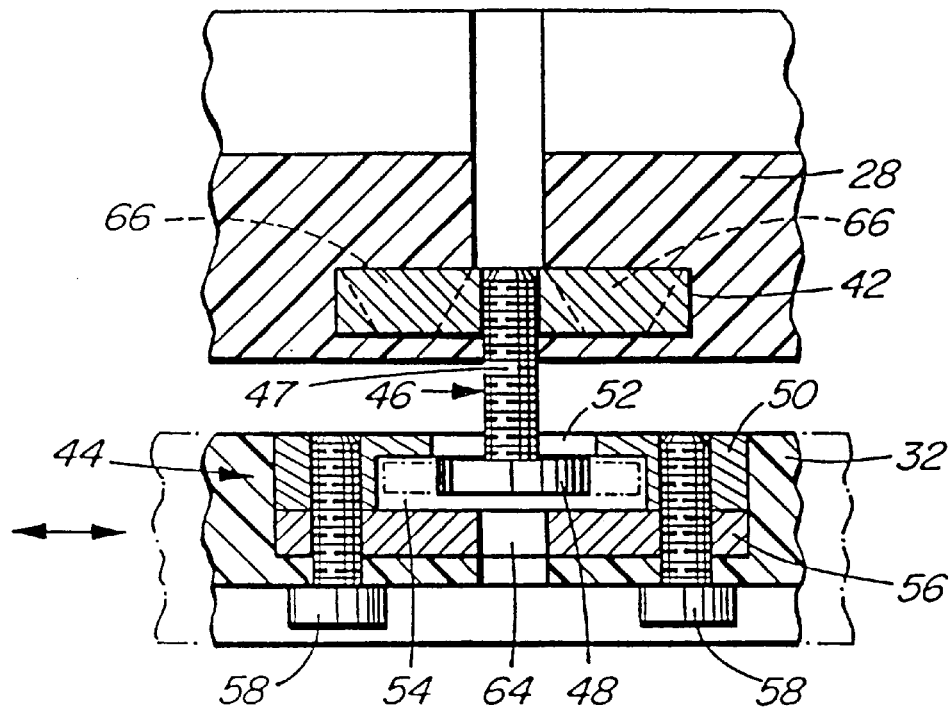
FIG. 9 is an enlarged, cross-sectional view taken along section lines 9—9 of FIG. 5 and looking in the direction of the arrows.

As shown best in FIGS. 3 and 9, bite blocks 28, 32 are united in an anterior region of appliance 20 by means of a connecting assembly generally designated 40. Assembly 40 includes a maxillary retention plate 42 which is bonded to upper bite block 28 in the anterior palatal region behind the central incisors and a mandibular guide box assembly 44 which is bonded to an anterior region of lower bite block 32. Retention plate 42 and guide box assembly 44 are preferably bonded to respective bite blocks 28,32 with heat-cureable dental acrylic. Retention plate 42 and guide box assembly 44 are connected by means of a stylus 46 as described further below. Stylus 46 preferably comprises a threaded portion 47 and an enlarged head 48.

Guide box assembly 44 consists of a guide box 50 having an elongated aperture 52 formed on its upper surface and a milled-out cavity 54 formed beneath aperture 50. Assembly 44 also includes a base plate 56 which may be releasably fastened to guide box 50 with screws 58. Screws 58 extend through apertures 60 formed in plate 56 and are received in internally threaded apertures 62 formed on either side of guide box 50 which are alignable with apertures 60 (FIGS. 3 and 9).

Figure 8:
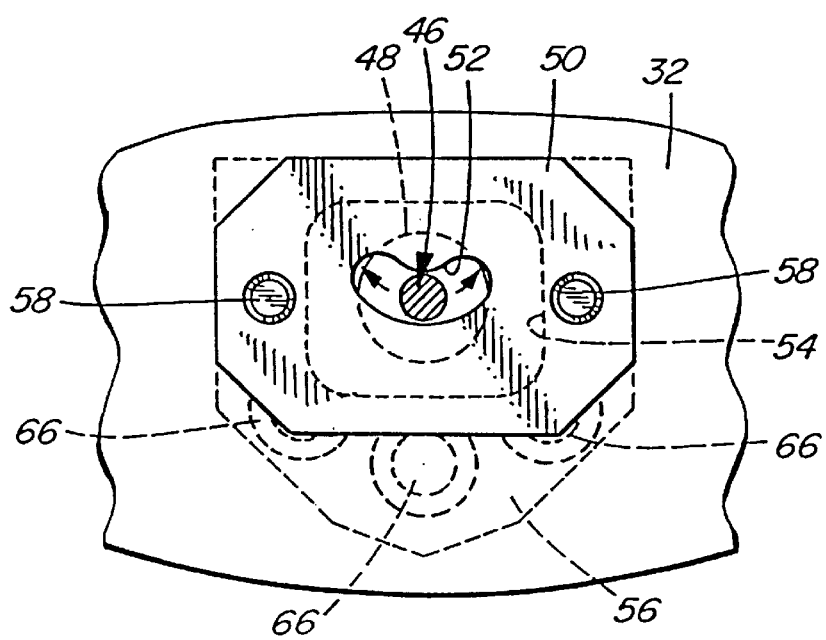
FIG. 8 is an enlarged, cross-sectional view taken along section lines 8—8 of FIG. 6 and looking in the direction of the arrows.

As shown best in FIG. 8, the elongated guide box aperture 52 is preferably kidney-shaped to correspond to the natural range of motion of the patient's jaw. Guide box 50 is positioned so that the convex curvature of aperture 52 faces forwardly.

As best shown in FIG. 3, the threaded portion 47 of stylus 46 is inserted through guide box aperture 52 before guide box 50 and base plate 56 are fastened together as aforesaid. Since the diameter of the stylus head 48 is larger than aperture 52, the stylus head 48 is effectively captured within the cavity 54 formed in guide box 50. Cavity 54 is sufficiently large to permit stylus head 48 to move vertically and laterally to a limited extent.

Figure 10:
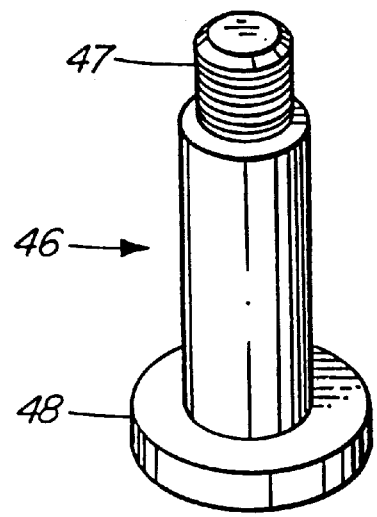
FIG. 10 is an enlarged, isometric view of an alternative embodiment of the stylus of the connecting assembly.

FIG. 10 illustrates an alternative embodiment of stylus 46. In this embodiment, only an end portion 47 of the stylus shaft is threaded. The remainder of the shaft is of a larger diameter than threaded portion 47 and is smooth and continuous. This ensures that the main body of the shaft will slide freely against the edge of guide box aperture 52 during nocturnal jaw movements.

Stylus 46 may be manufactured in different lengths to accommodate different dental configurations. The preferred overall lengths of stylus 46 vary between 6.8–9.8 mm.

Base plate 56 has a central aperture 64 to allow access to stylus head 48 (FIG. 9). Accordingly, stylus 46 can be manually turned using a screwdriver or some other suitable tool after guide box 50 and base plate 56 have been fastened together.

Base plate 56 also includes a plurality of countersunk, spaced-apart retention apertures 66. Retention apertures 66 are provided to allow dental acrylic to flow upwardly through base plate 56 to facilitate bonding of guide box assembly 44 to the lower bite block 32. Apertures 66 are countersunk to increase the surface area available for bonding. Preferably, the base plate 56 is larger than guide box 50 so that the dental acrylic flowing through retention apertures 66 will surround the perimeter of guide box 50, as best shown in FIG. 7.

Figure 7:
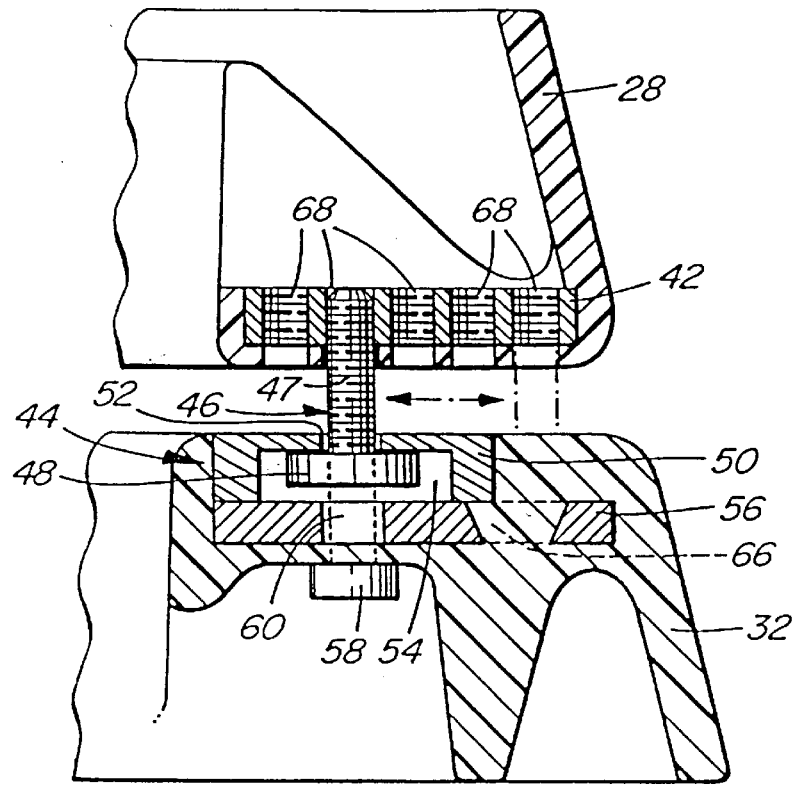
FIG. 7 is an enlarged, cross-sectional view taken along section lines 7—7 of FIG. 6 and looking in the direction of the arrows.

As best shown in FIGS. 3, 4 and 7, maxillary retention plate 42 includes a series of internally threaded apertures 68 which are spaced apart at regular intervals. Apertures 68 are provided for receiving the threaded portion 47 of stylus 46. Maxillary retention plate also includes a plurality of retention apertures 66 to allow the acrylic to flow through plate 42 to facilitate its bonding to upper bite block 28.

Preferably maxillary retention plate 40 and guide box assembly 44 are constructed from commercially pure titanium or some other metal which is non-reactive with oral fluids. Stylus 46 and screws 58 are preferably fabricated from titanium or stainless steel.

Dental appliance 20 is custom-fitted to suit the requirements of each individual patient. Usually the first step in the fitting procedure is for the dentist or physician to assess the natural range of motion of the patient's jaw and the likely degree of pharyngeal occlusion. This may be determined by physical examinations, sleep studies, x-rays and the like.

Molds of the patient's existing maxillary and mandibular dentition 30, 34 are then taken to enable casting of U-shaped bite blocks 28, 32. As indicated above, bite blocks 28, 32 are preferably formed of an elastomeric material. Dental wires 36 are embedded in bite blocks 28, 32 to provide structural stability. Opposing pairs of bite pads 38 are formed on the undersurface of upper bite block 28 and the upper surface of lower bite block 32 in a posterior region of appliance 20 (FIGS. 3 and 5). Bite pads 38 are constructed from hard dental acrylic and are provided to limit closure of the patient's jaw and prevent overeruption of the posterior teeth.

After bite blocks 28, 32 have been fabricated as aforesaid, they are united by means of connector assembly 40 (FIG. 3). Guide box 44 and stylus 46 of assembly 40 are loosely coupled together as described above so that the threaded portion 47 of stylus 46 protrudes upwardly through the elongated aperture 52 formed in guide box 50 (FIG. 3).

Retention plate 42 is bonded to the undersurface of upper bite block 28 and guide box assembly 44 is bonded to the upper surface of bite block 32 by means of heat-cureable dental acrylic. The soft acrylic flows through retention apertures 66 formed on retention plate 42 and base plate 56 to ensure that connecting assembly 40 is securely set in place as the acrylic hardens. As explained above, retention apertures 66 are countersunk to increase the surface area available for bonding to the dental acrylic.

After dental appliance 20 has been fabricated as described above, bite blocks 28, 32 are releasably coupled together by inserting the threaded portion 47 of stylus 46, which extends upwardly from guide box 50, into one of the mating apertures 68 formed in maxillary retention plate 42 (FIGS. 3, 7 and 9). Apertures 68 are spaced approximately 0.5 mm apart to allow the dentist or physician to make small adjustments in the relative position of bite blocks 28, 32 and hence the degree of anterior protrusion of the patient's mandible 22.

Preferably apertures 68 should be spaced to allow for a total adjustment range of approximately 7 mm. The inferior position of mandible 22 (i.e. the degree of opening of the jaw) may also be incrementally adjusted by varying the extent to which stylus 46 is screwed within a selected aperture 68. Stylus 46 may be turned with a screwdriver or other suitable tool insertable through base plate aperture 64 to engage stylus head 48.

In practice, appliance 20 is easily insertable within the mouth of a patient for wear during sleep. Appliance 20 is initially adjusted to advance mandible 22 between 25% and 75% of the patient's maximum protrusive capability. Typically approximately 5–8 millimetres of mandibular protrusion and approximately 4–6 millimetres of inferior opening are initially provided (FIG. 2). This is in contrast to some prior dental appliances where an inferior opening in the range of 10–20 millimetres is recommended. The inventor's studies suggest that in many patients the tongue 10 has a greater tendency to slide posteriorly as the degree of jaw opening increases. Displacement of the tempromandibular joint is also more likely if the jaw is fixed in a wide open position for long periods of time. Accordingly, dental appliance 20 is set to open the jaw the minimum amount possible while still allowing the patient to breathe comfortably through the mouth.

Opposed bite pads 38 formed on bite blocks 28, 32 provide a stop to complete closure of the jaw as best shown in FIGS. 4 and 6. This prevents overeruption of the posterior teeth during the wearing of appliance 20 and provides support to the tempromandibular joint and associated ligaments and muscles.

After the patient has been fitted with dental appliance 20 he or she is carefully monitored to determine if further adjustments are required. For example, if the patient's snoring or apnea episodes have not been completely eliminated, then the degree of mandibular protrusion may be incrementally increased by unscrewing stylus 46 from its initial setting, advancing lower bite block 32 forwardly, and inserting stylus 46 into an adjacent aperture 68 formed on maxillary retention plate 42 (FIG. 7). The degree of inferior opening of the mandible 22 can also be readily adjusted to suit the needs of a particular patient by altering the extent to which the threaded portion 47 of stylus 46 is screwed within a selected aperture 68. If the patient experiences discomfort from wearing appliance 20, then the dentist or physician can readily adjust the lower bite block 28 to a more retruded and/or a less inferior position.

A key feature of the applicant's invention is that connecting assembly 40 allows a limited degree of lateral movement of the patient's mandible 20 relative to the upper jaw 24 while still maintaining mandible 20 in the preferred protruded position. While the upper threaded portion 47 of stylus 46 is fixed in a selected aperture 68 formed in maxillary retention plate 42, the stylus head 48 is not fixed relative to lower bite block 32. Rather, stylus head 48 is loosely captured within cavity 54 formed in guide box 50, as best shown in FIGS. 7–9. This allows lower bite block 32 and hence mandible 22 to travel in a lateral excursion relative to stylus 46 (i.e. in the direction of the arrows shown in FIGS. 6, 8 and 9). The extent of lateral travel of mandible 22 is restricted by the size of aperture 52 formed on the upper surface of guide box 50 and also the size of guide box cavity 54 (FIG. 8).

As best shown in FIGS. 3 and 8 and as discussed above, guide box aperture 52 is preferably kidney-shaped to correspond to the natural range of motion of the patient's jaw joint. In one embodiment of the invention, the size and shape of aperture 52 could be customized to suit the anatomy of each particular patient, such as by performing gothic arch tracings to determine the natural range of motion of the patient's jaw anatomy.

Prior art intra-oral devices which maintain mandible 22 in a fixed, protruded position can lead to serious side effects, particularly in patients prone to nocturnal bruxism (teeth grinding). Such prior art devices may result in displacement or aggravation of the patient's tempromandibular joint and associated muscles and ligaments. The applicant's dental appliance 20 effectively overcomes this problem by allowing a predetermined degree of lateral movement of mandible 22 in the protruded position, while still maintaining acceptable airway patency.

As will be apparent to those skilled in the art in the light of the foregoing disclosure, many alterations and modifications are possible in the practice of this invention without departing from the spirit or scope thereof For example, more than one connecting assembly 40 could be provided. Further, the connecting assembly or assemblies 40 could be mounted in a posterior rather than an anterior region of dental appliance 20. In another alternative embodiment, guide box assembly 44 could be inverted so that elongate aperture 52 is formed on a top plate covering the open upper end of a guide box defining internal cavity 54. Other equivalent means for loosely coupling stylus 46 to lower bite block 32 may also be envisaged. Accordingly, the scope of the invention is to be construed in accordance with the substance defined by the following claims.

What is claimed is:

1. A method of treating snoring and obstructive sleep apnea by adjustably maintaining a patient's mandible in a protruded position comprising the steps of:

(a) casting an upper bite block by taking a mold of the patient's maxillary dentition;

(b) casting a lower bite block by taking a mold of the patient's mandibular dentition;

(c) securing a first retention element to an undersurface of said upper bite block in an anterior region thereof;

(d) securing a second retention element to an upper surface of said lower bite block in an anterior region thereof, said second element comprising an upwardly projecting connector having a lower end loosely captured within a cavity formed in said second element;

(e) determining the preferred degree of mandibular protrusion required to alleviate the patient's sleep apnea and snoring symptoms; and (f) releasably securing an upper end of said connector to said first retention element at a fixed position corresponding to the patient's preferred degree of mandibular protrusion as determined in step (e).

2. The method of claim 1, further comprising the steps of:

(a) tracing the natural range of motion of the patient's jaw anatomy; and (b) forming an aperture in said second element having a size and shape corresponding to said tracing, said aperture providing an opening for said cavity through which said connector projects, said aperture enabling a limited degree of lateral movement of said lower bite block relative to said upper bite block in said protruded position.

3. A method of treating snoring and obstructive sleep apnea by adjustably maintaining a patient's mandible in a protruded position comprising the steps of:

(a) providing an upper bite block conforming to the patient's maxillary dentition;

(b) providing a lower bite block conforming to the patient's mandibular dentition;

(c) providing a connector for releasably coupling said upper and lower bite blocks together;

(d) estimating the preferred degree of mandibular protrusion required to alleviate the patient's sleep apnea and snoring symptoms; and (e) releasably coupling said lower bite block to said upper bite block with said connector at a position corresponding to the patient's preferred degree of mandibular protrusion as determined in step (d), wherein said connector is slidably coupled to one of said upper and lower bite blocks to permit a limited degree of sliding movement of said lower bite block relative to said upper bite block in said protruded position.

4. A method of treating snoring and obstructive sleep apnea by adjustably maintaining a patient's mandible in a protruded position comprising the steps of:

(a) providing a dental appliance comprising an upper bite block conforming to the patient's maxillary dentition, a lower bite block conforming to the patient's mandibular dentition, and a connector for releasably coupling said upper and lower bite blocks together;

(b) estimating the preferred degree of mandibular protrusion required to alleviate the patient's sleep apnea and snoring symptoms; and (c) manually adjusting said connector until said lower bite block is at a position corresponding to the patient's preferred degree of mandibular protrusion as determined in step (b), and wherein said connector is slidably coupled to one of said upper and lower bite blocks to permit a limited degree of sliding movement of said lower bite block relative to said upper bite block in said protruded position.

5. The method of claim 4, further comprising fitting said dental appliance in said patient's oral cavity.

* * * * *